United States Patent [19]

Lin

[11] Patent Number: 5,454,812

[45] Date of Patent: Oct. 3, 1995

[54] SPINAL CLAMPING DEVICE HAVING MULTIPLE DISTANCE ADJUSTING STRANDS

[76] Inventor: Chih-I Lin, 513 S. Golden Pardos Dr., Diamond Bar, Calif. 10765

[21] Appl. No.: 340,445

[22] Filed: Nov. 14, 1994

Related U.S. Application Data

[63] Continuation of Ser. No. 151,018, Nov. 12, 1993, abandoned.

[51] Int. Cl.⁶ ................................................. A61B 17/70
[52] U.S. Cl. ................................................................ 606/61
[58] Field of Search .................................. 606/60, 61, 72, 606/73, 74, 103

[56] References Cited

U.S. PATENT DOCUMENTS 5,108,397  4/1992  White ......................................... 606/73

FOREIGN PATENT DOCUMENTS 322334  6/1989  European Pat. Off. ................. 606/61
1044278  9/1983  U.S.S.R. .................................... 606/61
1676605  9/1991  U.S.S.R. .................................... 606/61

*Primary Examiner*—Tamara L. Graysay
*Attorney, Agent, or Firm*—Bacon & Thomas

[57] ABSTRACT

A spinal clamping device includes a clamping member provided with a clamping portion and a connecting portion, a clamping adjusting member provided with a clamping portion and a connection portion, a distance adjusting cord of multiple strands, and a cord restraining member. The connecting portions of the clamping member and the clamping adjusting member are provided respectively with one or more cord receiving holes. Each of the multiple strands of the distance adjusting cord has one end that is fastened to the cord receiving hole and another end that is fastened with the cord restraining member. Each of the multiple strands passes through or loops the cord receiving hole of the clamping adjusting member for adjsuting the distance between the clamping member and the clamping adjusting member. The multiple strands of the distance adjusting cord are substantially on a same plane and parallel to one another.

8 Claims, 3 Drawing Sheets

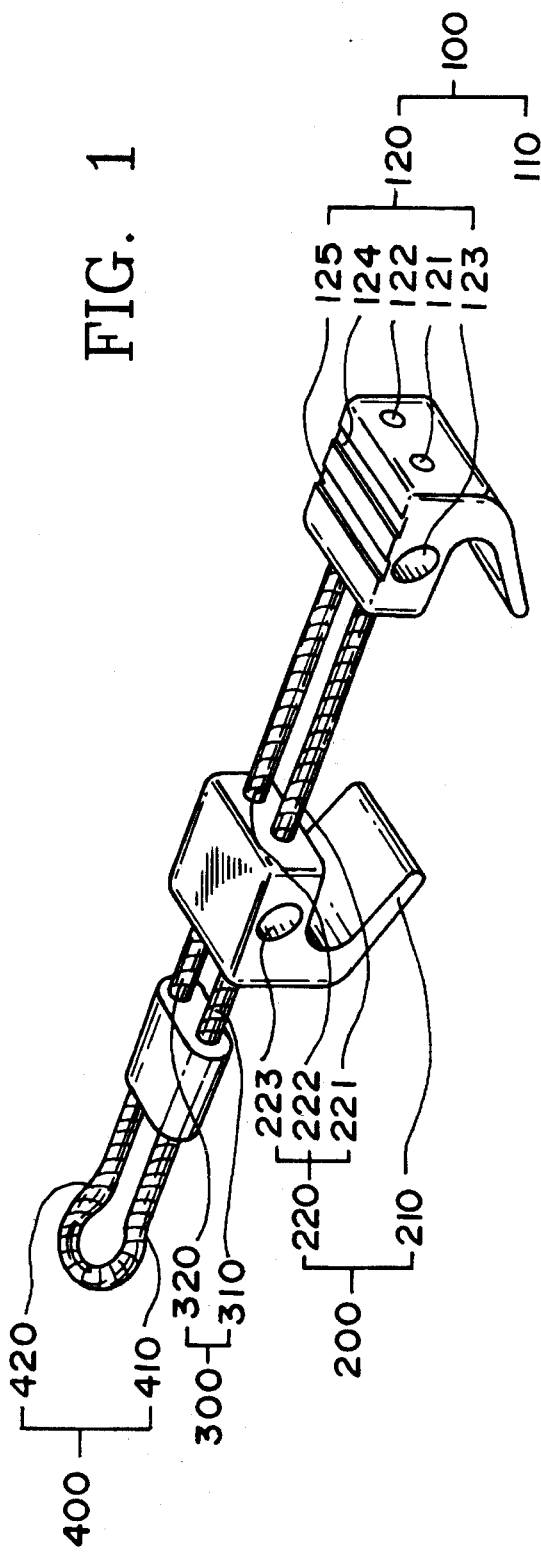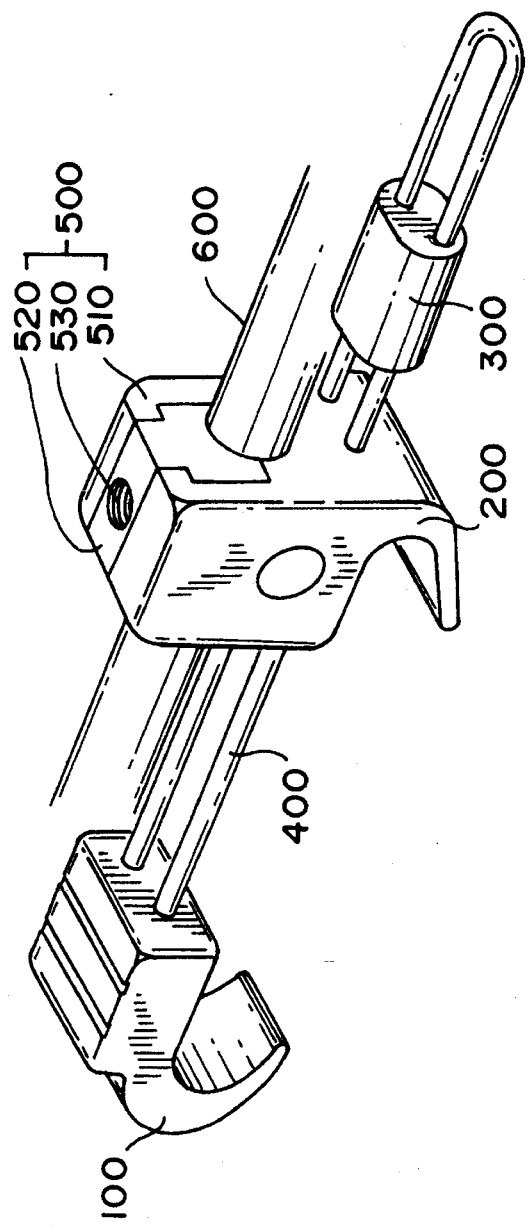

SPINAL CLAMPING DEVICE HAVING MULTIPLE DISTANCE ADJUSTING STRANDS

This application is a continuation of application Ser. No. 08/151,018, filed Nov. 12,1993, now abandoned.

FILED OF THE INVENTION

The present invention relates to a spinal clamping device having multiple distance adjusting strands.

BACKGROUND OF THE INVENTION

The spinal clamping device of the prior art is generally composed of a pair of hooked means intended for clamping a deformed vertebra under treatment, as exemplified by the HALIFAX™ interlaminar clamp system made by the AME Corp. of the United States. Such conventional spinal clamping device as described above is defective in design in that it often fails to fix and retrieve the deformed vertebra view of the fact that its hooked means are fastened by the nuts, which are vulnerable to becoming loosened by various movements of the clamped vertebra. The shortcoming of the spinal clamping device of the prior art described above was also pointed out by Ronald Moskovich in his article entitled "Altantoaxial Arthrodesis Using Interlaminar Clamps", which was published in SPINE, 17(3), 261(1992). For more details, please refer to FIG. 5 and the text thereof in Moskovich's article mentioned above.

In addition, the spinal clamping device of the prior art mentioned above can not be used as an auxiliary fixation device between the two vertebral locking rods.

With a view to overcoming the drawbacks of the aforementioned spinal clamping device of the prior art, this inventor has disclosed in the pending U.S. patent applications Ser. Nos. 08/004,612 (filing date: Jan. 14, 1993) now abandoned and 08/004,610 (filing date: now Jan. 14,1993 now U.S. Pat. No. 5,352,225 a two-layered spinal clamping system, in which the adjustment of the distance between the two hooked means is attained by means of the screws engageable with the threaded slots of a flat plate. In addition, this inventor has further disclosed in the pending U.S. patent application Ser. No. 08/004,609 (filing date: Jan. 14, 1993) now abandoned a spinal clamping system in which the distance between the two hooked means of the system is adjusted by making use of a plurality of bevel hooking slots of a hooking member capable of retaining reversibly. However, these improved spinal clamping systems disclosed in the above-mentioned U.S. patent application are limited in that the distance between the two hooked means can not be adjusted at will and that the systems are not as effective as expected in locking and retrieving a deformed vertebra.

SUMMARY OF THE INVENTION

It is therefore the primary objective of the present invention to provide a spinal clamping device having multiple parallel strands.

A further objective of the present invention is to provide a spinal clamping device having multiple strands, which comprises a clamping member, a clamping adjusting member, a cord restraining member, and a distance adjusting cord of multiple strands.

In keeping with the principles of the present invention, the foregoing objectives of the present invention are accomplished by the spinal clamping device having multiple strands, which comprises a clamping member, a clamping adjusting member, a distance adjusting cord of multiple strands, and a cord restraining member.

The clamping member comprises a clamping portion and a connecting portion which is provided with one or more cord receiving holes.

The clamping adjusting member comprises a clamping portion and a connecting portion which is provided with one or more cord receiving holes.

The distance adjusting cord of multiple strands has a fixing end and an adjusting end. The fixing end is fastened to the cord receiving hole of the clamping member. The adjusting end of said distance adjusting cord is put through or looped in the cord receiving holes of the clamping adjusting member and is intended for use in adjusting the distance between the clamping member and the clamping adjusting member.

The cord restraining member is joined with the adjusting end of the distance adjusting cord and is intended for averting an unintentional change in the distance between the clamping member and the clamping adjusting member.

The present invention is characterized in that the multiple strands of the distance adjusting cord are arranged on a same plane and are substantially parallel to one another.

The foregoing objectives, structures, features and functions of the present invention can be more readily understood by studying the following detailed description of the present invention in conjunction with the accompanying drawings.

BRIEF DESCRIPTION OF THE DRAWINGS

FIG. 1 shows a perspective view of a preferred embodiment of the present invention.

FIG. 3 is a schematic view showing the present invention employed in cooperation with a spinal locking rod and a clamping device for retaining the spinal locking rod.

DETAILED DESCRIPTION OF THE INVENTION

Figure 2A:
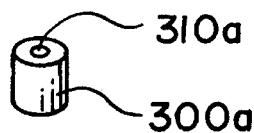
FIGS. 2a–2l show schematic views of each constituent part of the preferred embodiment of the present invention.

As shown in FIG. 1, the preferred embodiment of the present invention comprises a clamping member 100, a clamping adjusting member 200, a cord restraining member 300, and a distance adjusting cord 400 of dual strands.

The clamping member 100 is composed of a clamping portion 110 and a connecting portion 120 which is provided with two cord receiving holes 121 and 122, a tool hole 123, and two punched slots 124 and 125.

The clamping adjusting member 200 consists of a clamping portion 210 and a connecting portion 220 which is provided with two cord receiving holes 221 and 222, and a tool hole 223.

The cord restraining member 300 is provided with two cord receiving and locking holes 310 and 320.

The distance adjusting cord 400 has two strands 410 and 420, which are received and held respectively in the two cord receiving and locking holes 310 and 320 of the cord restraining member 300, the two cord receiving holes 221 and 222 of the clamping adjusting member 200, and the two cord receiving holes 121 and 122 of the clamping member 100. The two strands 410 and 420 of the distance adjusting cord 400 are fixed finally and respectively in the clamping member 100 by the punched slots 124 and 125. In surgical operation, the clamping portion 110 of the clamping member 100 and the clamping portion 210 of the clamping adjusting member 200 are used to clamp firmly two vertebrae intended to be fixed or two vertebral locking rods. The tools are then inserted respectively into the tool holes 123 and 223 of the connecting portions 120 and 220 of the clamping member 100 and the clamping adjusting member 200. Thereafter, the distance between the clamping member 100 and the clamping adjusting member 200 is adjusted appropriately before the distance adjusting cord 400 is tightened. The cord restraining member 300 is subsequently forced to move toward the clamping adjusting member 200 until the cord restraining member 300 is in a close contact with the clamping adjusting member 200. The cord restraining member 300 is then bent or deformed by means of a hand tool so as to ensure that the distance adjusting cord 400 is fixed inside the two cord receiving and locking holes 310 and 320 appropriately.

Figure 2B:
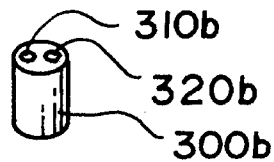
Figure 2C:
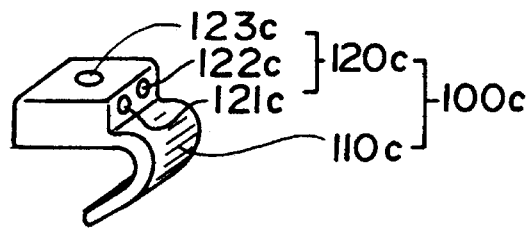
Figure 2D:
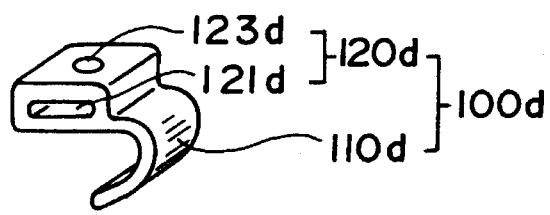
Figure 2E:
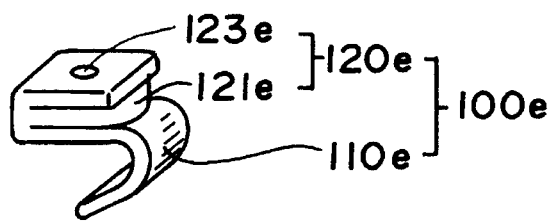
Figure 2F:
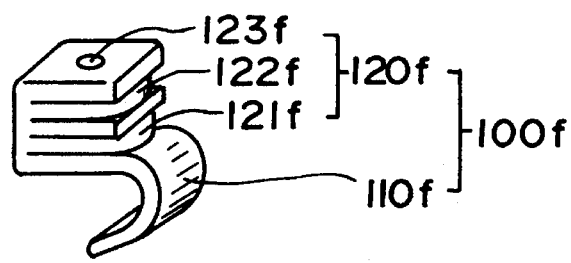
Figure 2G:
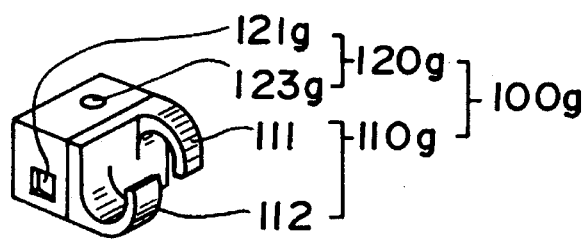
Figures 2H, 2I, 2J, 2K, 2L:
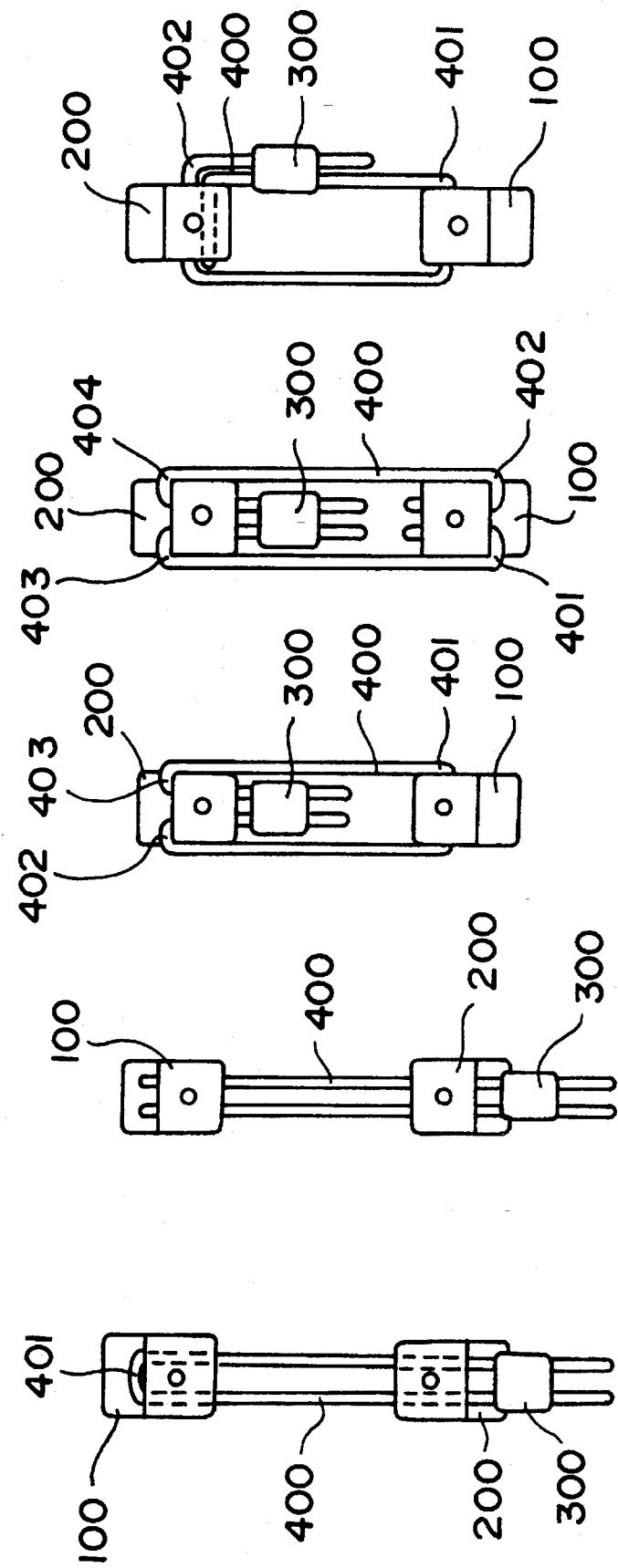

Now referring to FIGS. 2a–2l in which all reference numerals are similar in definition to those of FIG. 1. It is shown in FIGS. 2a and 2b that the cord restraining member 300a and 300b can have one and two cord receiving and locking holes 310a and 310b, 320b respectively. In FIG. 2c, the clamping member 100a has two through holes 121a and 122a as the cord receiving holes, while in FIG. 2d, the two cord receiving holes 121c and 122c in FIG. 2c become a cross hole 121d. As shown in FIG. 2e, the cord receiving holes 121 and 122 in FIG. 2c. become a single cord receiving slot 121e. On the other hand, in FIG. 2f, there are two cord receiving slots 121f and 122f. It is shown in FIG. 2g that there is a cross hole 121g and that the clamping portion 110g has dual retaining hooks 111 and 112. In FIGS. 2c–2g, the tool hole 123c–123g respectively can be fastened with an auxiliary fixation device. The clamping member 100c–100g respectively shown in FIGS. 2c–2g may be contemplated as the clamping adjusting member 200. In FIGS. 2h–2l, the clamping member 100, the clamping adjusting member 200, the cord restraining member 300, and the distance adjusting cord 400 are shown to be joined together in various ways. FIG. 2h shows one distance adjusting cord, one loop, and the cord restraining member being outside a space defined by the clamping member and the clamping adjusting member. FIG. 2i shows two distance adjusting cords, no loop, and the cord restraining member being outside a space defined by the clamping member and the clamping adjusting member. FIG. 2j shows one distance adjusting cord, three loops, and the cord restraining member being situated between the clamping member and the clamping adjusting member. FIG. 2k shows two distance adjusting cords, four loops, and the cord restraining member being situated between the clamping member and the clamping adjusting member. FIG. 2l shows one distance adjusting cord, two loops, and the cord restraining member being situated on one side of the line connecting the clamping member and the clamping adjusting member. It must be noted here that the word "loop" refers to the manner in which the distance adjusting cord is made a U-turn around or "looped" the clamping member 100 or the clamping adjusting member 200, such as 401 of FIG. 2h; 401, 402 and 403 of FIG. 2j; 401, 402, 403 and 404 of FIG. 2k; and 401 and 402 of FIG. 2l. On the basis of a preliminary analysis, it is believed that a spinal clamping device having multiple distance adjusting cords has a superior fixing effect compared to a spinal clamping device having one distance adjusting cord of multiple strands. A better fixing effect can be expected if the cord restraining member is situated outside a space defined by the clamping member and the clamping adjusting member, i.e. the ones shown in FIGS. 2h and 2i. It is believed that a better fixing effect can be accomplished by the present spinal clamping device if the number of the "loop"s is smaller, e.g. the spinal clamping device shown in FIG. 2i.

The spinal clamping device of the present invention can be put to use in cooperation with a spinal locking rod 600 and a locking rod clamping device 500, as shown in FIG. 3. The spinal locking rod 600 is joined with vertebrae to be fixed. The vertebrae are not shown in FIG. 3. The spinal locking rod 600 is fastened with the clamping adjusting member 200 by the locking rod clamping device 500 which is provided with an outer clamping block 510, an inner clamping block 520 and an external connecting hole 530 intended for use in fastening thereto an auxiliary fixation device. For more details, please refer to a pending U.S. patent application Ser. No. 08/151,016 filed on Nov. 12, 1993, now U.S. Pat. No. 5,380,326 by this inventor.

For a better fixing effect, it is suggested that the clamping portion 110 and the connecting portion 120 of the clamping member 100 are made integrally, and that the clamping portion 210 and the connecting portion 220 of the clamping adjusting member 200 are also made integrally. The connecting portions 120 and 220 are provided respectively with one or more cord receiving holes, which may be furrows, slots, through holes, or cross holes, as shown in FIGS. 2c–2g. If necessary, the connecting portions 120 and 220 may be fastened respectively with an additional spinal locking device or an auxiliary fixation device. The clamping portion 110 of the clamping member 100 may be composed of one hook or multiple hooks. Similarly, the clamping portion 210 of the clamping adjusting member 200 may consist of one hook or multiple hooks.

The cord restraining member may be provided with one cord receiving hole 310a, as shown in FIG. 2a, or two cord receiving holes 310b and 320b, as shown in FIG. 2b. If the cord restraining member is provided with one cord receiving hole 310a, the distance adjusting cord 400 is put through hole 310a is varied. Thereafter, the position of the cord restraining member 300 on the distance adjusting cord 400 must be adjusted appropriately so that the clamping member 100 and the clamping adjusting member 200 are spaced at an appropriate interval. The position of the cord restraining member 300 on the distance adjusting cord 400 is then fixed by bending or deforming the cord restraining member 300 with a hand tool.

If the clamping member 100 or the clamping adjusting member 200 is provided with through holes or horizontal holes serving as cord receiving holes, the distance adjusting cord 400 is joined at a fixing end thereof with the clamping member 100 or at an adjusting end thereof with the clamping adjusting member 200 in such a manner that the distance adjusting cord 400 is put through the through holes or the horizontal holes mentioned above. If the clamping member 100 or the clamping adjusting member 200 is provided with slots serving as cord receiving holes, the distance adjusting cord 400 is joined with the clamping member 100 or the clamping adjusting member 200 in such a way that the distance adjusting cord 400 is looped in the slots, as shown in FIGS. 2g–2k.

The distance adjusting cord 400 of the present invention may be a single cord of multiple strands or multiple cords of single strand. If the distance adjusting cord 400 is a single cord of multiple strands, it is put through the cord receiving holes of the clamping member 100 or the clamping adjusting member 200 and looped to form another strand. If the distance adjusting cord 400 is composed of multiple cords of single strand, each of the multiple cords serves independently as a strand, as shown in FIGS. 2h–2l. The distance adjusting cord 400 of the present invention serves to connect the clamping member 100 with the clamping adjusting member 200, to adjust the distance between the clamping member 100 and the clamping adjusting member 200, and to allow the clamping member 100 and the clamping adjusting member 200 to be situated on different planar surfaces so that the clamping member 100 or the clamping adjusting member 200 can be adjusted freely to fasten with a vertebra or a spinal locking rod in a desired direction, position and point of application. Such advantages inherent in the distance adjusting cord 400 of the present invention as described above are also discussed in detail on pages 20–25 of OPERATIVE SPINAL SURGERY by M. J. Torrens and R. A. Dickson, which was published by Churchill Livingstone in 1991.

The spinal clamping device of the present invention can be used to fix and retrieve two deformed vertebrae. In addition, the spinal clamping device of the present invention can be employed to fix one deformed vertebra and one spinal locking rod simultaneously. In other words, the spinal clamping device of the present invention can be used to achieve effectively an auxiliary fixation of a deformed vertebra or a horizontal auxiliary fixation of a deformed vertebra. Furthermore, the spinal clamping device of the present invention is an ideal surgical device for use in locking and retrieving a deformed vertebra in cooperation with other spinal fixation systems in existence.

What is claimed is:

1. A spinal clamping device comprising:

a clamping member comprising a clamping portion and a connecting portion which is provided with a cord receiving means;

a clamping adjusting member comprising a clamping portion and a connecting portion which is provided with another cord receiving means, the clamping portion of said clamping member and the clamping portion of said clamping adjusting member being adapted to clamp a predetermined number of vertebra therebetween;

multiple distance adjusting strands, each of which has one end serving as a fixing end and another end serving as an adjusting end, said fixing end of each of said multiple distance adjusting strands being fastened to said cord receiving means of said clamping member, and with said adjusting end of each of said multiple distance adjusting strands being received by said cord receiving means of said clamping adjusting member, said clamping adjusting member being slidably movable relative to said clamping member along said multiple distance adjusting strands in order to position said clamping adjusting member a desired distance from said clamping member; and cord restraining means joined with said adjusting end of each of said multiple distance adjusting strands for maintaining the desired distance between said clamping member and said clamping adjusting member by fixedly interconnecting said multiple distance strands together directly adjacent said clamping adjusting member;

wherein said multiple distance adjusting strands are arranged such that said multiple distance adjusting strands are substantially located in a single plane and parallel to one another.

2. The spinal clamping device of claim 1 wherein said multiple distance adjusting strands is composed of a single distance adjusting cord of multiple strands.

3. The spinal clamping device of claim 2 wherein said single distance adjusting cord of multiple strands extends through the cord receiving means of said clamping member and the cord receiving means of said clamping adjusting member.

4. The spinal clamping device of claim 3 wherein said cord restraining means is located between said clamping member and said clamping adjusting member.

5. The spinal clamping device of claim 3 wherein said cord restraining means is located outside a planar surface defined by said clamping member, said clamping adjusting member and said distance adjusting strands.

6. The spinal clamping device of claim 1 wherein said multiple distance adjusting strands is composed of multiple single distance adjusting cords of single strand.

7. The spinal clamping device of claim 1 wherein said cord restraining means is located between said clamping member and said clamping adjusting member.

8. The spinal clamping device of claim 1 wherein said cord restraining means is located outside a space defined by said clamping member and said clamping adjusting member.

* * * * *